US010799448B2

(12) United States Patent
Ito et al.

(10) Patent No.: US 10,799,448 B2

(45) Date of Patent: Oct. 13, 2020

(54) THERAPEUTIC EFFECT OF ORAL INTERFERON A ADMINISTRATION ON CHRONIC INTRACTABLE EXTERNAL OTITIS

(71) Applicants: National Institute of Advanced Industrial Science and Technology, Tokyo (JP); Hokusan Co. Ltd, Hokkaido (JP)

(72) Inventors: Akira Ito, Hokkaido (JP); Takeshi Matsumura, Hokkaido (JP); Toru Gotanda, Hokkaido (JP); Noriko Tabayashi, Hokkaido (JP); Noriko Itchoda, Hokkaido (JP); Takashi Aoki, Hokkaido (JP); Uiko Kagaya, Hokkaido (JP)

(73) Assignees: NATIONAL INSTITUTE OF ADVANCED INDUSTRIAL SCIENCE AND TECHNOLOGY, Tokyo (JP); HOKUSAN CO. LTD, Kitahiroshima-shi (JP)

( * ) Notice: Subject to any disclaimer, the term of this patent is extended or adjusted under 35 U.S.C. 154(b) by 54 days.

(21) Appl. No.: 15/562,870

(22) PCT Filed: Jan. 12, 2016

(86) PCT No.: PCT/JP2016/050727

§ 371 (c)(1),
(2) Date: Sep. 28, 2017

(87) PCT Pub. No.: WO2016/157929

PCT Pub. Date: Oct. 6, 2016

(65) Prior Publication Data

US 2019/0029953 A1 Jan. 31, 2019

(30) Foreign Application Priority Data

Mar. 31, 2015 (JP) ................................ 2015-073774

(51) Int. Cl.

| | |
|---|---|
| ***A61K 9/00*** | (2006.01) |
| ***A61K 38/21*** | (2006.01) |
| ***A61P 27/16*** | (2006.01) |
| ***A61K 9/20*** | (2006.01) |
| ***A23L 33/00*** | (2016.01) |
| ***A61K 9/68*** | (2006.01) |

(52) U.S. Cl.

CPC ............ *A61K 9/0053* (2013.01); *A23L 33/00* (2016.08); *A61K 9/0056* (2013.01); *A61K 9/0058* (2013.01); *A61K 9/20* (2013.01); *A61K 38/212* (2013.01); *A61P 27/16* (2018.01)

(58) Field of Classification Search

None

See application file for complete search history.

(56) References Cited

U.S. PATENT DOCUMENTS

2010/0202982 A1* 8/2010 Yoshioka ............ A61K 9/0063 424/49
2011/0275602 A1* 11/2011 Massari ................ A61K 45/06 514/171

FOREIGN PATENT DOCUMENTS

JP 10-273448 A 10/1998
WO 2007/080942 A1 7/2007

OTHER PUBLICATIONS

Takayama et al., Am. Journal of the Medical Sciences, 309(5), p. 282-284: abstract only (Year: 1995).*
Butterfield et al.,Leukennia Research 36, p. 192-197 (Year: 2012).*
Kimata et al, "Interferon-alpha treatment for severe atopic dermatitis," Allergy, 1995, vol. 50, pp. 837-840.
Nishifuji et al., "A case of Hyperplastic Dermatosis of the West Highland White Terrier Controlled by Recombinant Canine Interferon-γ Therapy," J. Vet. Med. Sci., 2007, vol. 69, No. 4, pp. 455-457.
Pung et al., "Use of interferons in atopic (IgE-mediated) diseases," Annals of Allergy, Sep. 1993, vol. 71, pp. 234-238.
Iwasaki, T., "Inu no Atopic Hifuen no Chiryo to Kanri ni Tsuite", MP Agro Journal, Jul. 2012, No. 10, pp. 4-9.
Kano, R., "Update Review on Malassezia Pachydermatis and Malassezia Dermatitis in Dogs," Japanese Society of Veterinary Dermatology, 2014, vol. 19, No. 3, pp. 131-134.
Kawaguchi, Y., "Successful Treatment of Canine Atopic Dermatitis with Severe Malassezia Overgrowth in a West Highland White Terrier by Canine Recombinant Interferon Gamma," Japanese Society of Veterinary Dermatology, 2013, vol. 20, No. 3, pp. 161-163.
Nosai, K., "Idenshi Kumikae Ichigo de Dobutsu-yo Iyakuhin o Kaihatsu," Feb. 2014, No. 604, pp. 1-2.

(Continued)

*Primary Examiner* — Joanne Hama
*Assistant Examiner* — Jegatheesan Seharaseyon
(74) *Attorney, Agent, or Firm* — Kilpatrick Townsend & Stockton LLP

(57) ABSTRACT

The object of the present invention is to provide a therapeutic agent illustrating an immediate and sustained effect on chronic intractable external otitis. The present invention provide a composition, pharmaceutical composition, food and feed for preventing and/or treating chronic intractable external otitis, each comprising interferon-α (IFNα) as an active ingredient. Orally administering the composition of the present invention can provide inhibition, alleviation, treatment and prevention for chronic intractable external otitis. According to the present invention, IFNα can give a sufficient effect even when administered in a very small amount.

6 Claims, 5 Drawing Sheets

Specification includes a Sequence Listing.

(56) References Cited

OTHER PUBLICATIONS

Shinma et al., "Open innovation hub in AIST," Folia Pharm. acologica Japonica, 2014, vol. 143, No. 6, pp. 295-301.
Tabayashi et al., "Idenshi Kumikae Ichigo o Gen'yaku to suru Dobutsuyaku no Kaihatsu," Journal of the Society for Bioscience and Bioengineering , Japan, 2014, vol. 92, No. 10, pp. 537-539.

* cited by examiner

Lane C: non-transgenic strawberry,
Lanes 1 to 13: CaIFNα-4 transgenic strawberry,
Lane P: plasmid vector,
Lane M: size marker 100bp DNA ladder Negative control
Non-transgenic strawberry
CaIFNα -4(−)
CPE:Positive Transgenic strawberry
CaIFNα -4(+)
CPE:Negative Positive control
Baculovirus Expression
CaIFNα -4
CPE:Negative External ear
of control group
(21d)
No13
Cerumen+/redness+
No14
Cerumen+/redness+
/bad odor+
No18
Cerumen+/redness+
/bad odor+/pruritus+
Cerumen of each individual
(control group)
External ear
of treated group
(21d)
No15
Cerumen+
No16
Healing
No17
Healing
Cerumen of each individual
(treated group)

THERAPEUTIC EFFECT OF ORAL INTERFERON A ADMINISTRATION ON CHRONIC INTRACTABLE EXTERNAL OTITIS

CROSS-REFERENCE TO RELATED APPLICATIONS

The present application is a National Phase entry of International Application No. PCT/JP2016/050727, filed Jan. 12, 2016, which claims priority to Japanese Patent Application No. 2015-073774, filed Mar. 31, 2015, the disclosures of which are hereby incorporated by reference in their entireties for all purposes.

TECHNICAL FIELD

The present invention relates to a composition for oral administration for preventing and/or treating chronic intractable external otitis, the composition comprising interferon-α as an active ingredient.

BACKGROUND ART

External otitis is a very common disease and develops in pets such as dogs and cats with a very high morbidity rate. External otitis, when it became chronic, is also one of diseases that are very difficult for veterinarians and owners to effectively treat. The treatment strategy is widespread and uses various drugs for treating external otitis. For external otitis, in general, symptomatic treatments with anti-inflammatory agents and antimicrobial agents are carried out, but preventive treatments are not carried out at present.

In recent years, canine external otitis has been recognized as a skin disease in the broad sense. It has been reported that in the case of Malassezia external otitis, for example, the barrier of the external ear skin becomes fragile so that Malassezia, irrespective of being an indigenous bacterium, causes inflammation.

It has been reported that interferon (IFN) is provided for the treatment of skin diseases such as atopic dermatitis. For example, it has been reported that intravenous administration of human IFN-β for human atopic dermatitis illustrated certain effects on the dermatitis (Patent Literature 1). In non-human mammals, for example in cattle, feeding of human IFN-α with milk substitutes has been reported to illustrate effects on middle otitis (Non-patent Literature 1).

It has also been reported that subcutaneous injection of canine IFN-γ for canine intractable dermatitis resulted in improvement of the dermatitis (Patent Literature 2 and 3). Many of such existing interferon-containing preparations are generally invasively (subcutaneously or intravenously) administered at high concentration. However, complete recovery of chronic intractable external otitis such as Malassezia external otitis has been difficult, and agents illustrating an excellent prophylactic or therapeutic effect have not been found.

PRIOR ART DOCUMENTS

Patent Literature

[Patent Literature 1] Japanese Unexamined Patent Publication (Kokai) No. 6-48957

[Patent Literature 2] Japanese Unexamined Patent Publication (Kokai) No. 10-306037

[Patent Literature 3] Japanese Unexamined Patent Publication (Kokai) No. 2000-316585

Non-Patent Literature

[Non-patent Literature 1] AJVR, Vol. 66, No. 1, p. 164-176

DISCLOSURE OF THE INVENTION

Problems to be Solved by the Invention

Skin diseases often become chronic, and also often treated with the above-mentioned prior art repeatedly. For that reason, the diseases may need prolonged treatment for complete cure, or even may not reach complete cure. Therefore, a quick-acting and sustained therapeutic agent for chronic intractable external otitis, as a dermatitis which does not obtain complete cure even when treated with a therapeutic agent according to the prior art for a long period of time, is desired. Many of the conventional interferon preparations have been administered invasively at high concentration, whereas oral administration of interferon at low dose is expected to have advantages such as safety and ease of administration.

Means for Solving the Problems

The present inventors have found that oral administration of a composition containing interferon (IFN)-α as an active ingredient to a subject suffering from chronic intractable external otitis which is hardly cured by prior art provides a remarkable improvement of the disease, thereby completing the present invention. In other words, the present invention provides a composition and a pharmaceutical composition for oral administration (or for oral mucosal application or gingival application) for preventing and/or treating chronic intractable external otitis, the composition containing interferon-α as an active ingredient, and a method for preventing and/or treating chronic intractable external otitis.

In other words, the present invention is as follows.

[1] A composition for oral administration for preventing and/or treating chronic intractable external otitis, comprising interferon-α as an active ingredient.

[2] The composition described in [1], wherein the composition comprises interferon-α and a chewable carrier.

[3] The composition described in [2], wherein the chewable carrier is food.

[4] The composition described in [3], which is a chewable tablet or a chewing gum.

[5] The composition described in [1], comprising interferon-α and a paste carrier.

[6] The composition described in [1] to [5], wherein 0.5 to 25,000 LU/day/kg of body weight of interferon-α is compounded.

[7] A method for preventing and/or treating chronic intractable external otitis, the method including orally administering interferon-α.

[8] The method described in [7], including orally administering a composition containing interferon-α and a chewable carrier or a paste carrier.

[9] The method described in [8], wherein 0.5 to 25,000 LU/day/kg of body weight of interferon-α is orally administered.

[10] A pharmaceutical composition for preventing and/or treating chronic intractable external otitis, the pharmaceutical composition containing interferon-α and a pharmaceutically acceptable carrier.

[11] The pharmaceutical composition described in [10], wherein the pharmaceutically acceptable carrier is a chewable carrier or a paste carrier.

[12] The pharmaceutical composition described in [11], wherein 0.5 to 25,000 LU/day/kg of body weight of interferon-α is compounded.

[13] The use of interferon-α in manufacturing a composition for oral administration for treating and/or preventing chronic intractable external otitis.

Effects of the Invention

The composition for preventing and/or treating chronic intractable external otitis in mammals according to the present invention can be administered orally (or by oral mucosal application) to mammals to prevent and treat the external otitis.

MODE FOR CARRYING OUT THE INVENTION

Figure 1:
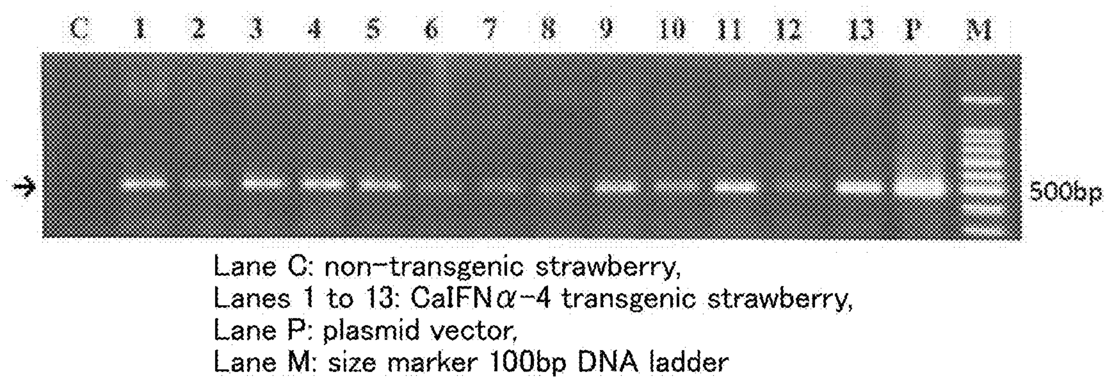
FIG. 1 illustrates a result of PCR confirming whether a CaIFNα-4 gene has been introduced into strawberries.

The present invention relates to a composition for oral administration, oral mucosal application or gingival application for preventing and/or treating chronic intractable external otitis, the composition comprising interferon-α as an active ingredient. The composition of the present invention can be produced by mixing IFNα and a biologically acceptable carrier.

Interferon (IFN) is a protein with a molecular weight of about 20 kDa that is secreted in the animal body upon viral infection or such. Mammals have three types of INFs: α, β, and γ. Of these, α and β are structurally similar to each other. For example, in human and mouse, a and p exhibit about 40% and 35% homology at the nucleotide and amino acid sequence levels, respectively. These IFNs are collectively called type-I IFN. In addition to the antiviral activity, type-I IFN has been found to have the following activities: cell growth-suppressing activity; antitumor activity; activity of activating immune cells such as macrophages; and immune response-regulating activity.

IFNα of mammals such as human and mouse are polymorphic. For example, a group of 15 or more homologous (85% or higher) genes have been found in human. The major characteristic of the IFNα gene is that it has no intron and exists in multiple copies as polymorphic variants in the genome.

The IFNα of the present invention includes all the subtypes derived from such polymorphic variants. In addition, proteins comprising an amino acid sequence with addition, deletion, substitution, or insertion of one or multiple amino acids in the amino acid sequence of such a subtype and having the biological activity equivalent to or higher than that of IFNα can also be used as IFNα of the present invention. IFNα derived from any animal species can be used as IFNα of the present invention. Preferably, canine IFNα can be used. More specifically, canine IFNα (hereinafter sometimes referred to as "CaIFNα-4") has an amino acid sequence (SEQ ID NO: 2) encoded by the nucleotide sequence represented by SEQ ID NO: 1.

Alternatively, IFNα derived from other species may be used as long as it can produce the effect of preventing and/or treating chronic intractable external otitis. For example, IFNα subtypes derived from the species listed below are known. The nucleotide and amino acid sequences of the respective subtypes of naturally-occurring IFNα are available under the GenBank accession numbers indicated below. In any species, there is a possibility that new subtypes will be discovered in addition to these subtypes. Any subtype newly identified in the future can also be used as IFNα of the present invention as long as it has the required activity.

In general, the amino acid sequences represented by these accession numbers contain signal sequences. When an amino acid sequence contains a signal sequence, a mature protein from which the signal sequence has been removed is used as IFNα of the present invention. If a precursor protein consisted of an amino acid sequence with the whole or a portion of signal sequence has IFNα biological activities, it can also be used as IFNα. Further, precursor proteins that can acquire IFNα biological activities when the whole or a portion of signal sequence is removed after administration can also be used as IFNα of the present invention.

Canine IFNα (8 subtypes)

CaIFN-a1:M28624 CaIFN-a2:M28625 CaIFN-a3: O97945 CaIFN-a4:AB102731 CaIFN-a5:AB125934 CaIFN-a6:AB125935 CaIFN-a7:AB125936 CaIFN-a8: AB125937

Feline IFNα (14 subtypes)

FeIFN-w:E02521 FeIFN-a1:AY117395 FeIFN-a2: AY117394 FeIFN-a3:AY117393 FeIFN-a5:AY117392 FeIFN-a6:AY117391 FeIFN-a7:AB094996 FeIFN-a8: AB094997 FeIFN-a9:AB094998 FeIFN-a10:AB094999 FeIFN-a11:AB095000 FeIFN-a12:AB095001 FeIFN-a13: AB095002 FeIFN-a14:AB095003

Rodent IFNα (8 subtypes)

D00460, M13660, M13710, X01969, X01971, X01972, X01973, X01974

Bovine IFNα (8 subtypes)

M10952, M10953, M10954, M10955, M11001, X93087, X93088, X93089

Porcine IFNα

IFN-a1: X57191.1

Human IFNα (21 subtypes)

HuIFN-a1:DQ185447 HuIFN-a2:NM000605 HuIFN-a3: E00176 HuIFN-a4:NM021068 HuIFN-a5:NM002169

HuIFN-a6:NM021002 HuIFN-a7:NM021057 HuIFN-a8: NM002170 HuIFN-a10:NM002171 HuIFN-a13: NM006900 HuIFN-a14:NM002172 HuIFN-a16: NM002173 HuIFN-a17:NM021268 HuIFN-a21: NM002175 HuIFN-a2a:AAS92248 HuIFN-a2b:AAP20099 HuIFN-a1b:AAL35223 HuIFN-a4b:CAA26701 HuIFN-aI': AAA52725 (=HuIFN-a17subtype) HuIFN-aI1:CAA01748 (=HuIFN-a17subtype) HuIFN-a-j:CAA23792 HuIFN-aT: I79343 HuIFN-aO:I79344 HuIFN-aN:I58999 HuIFN-aB: 0902162A For example, the preparations of human IFN listed below have also been put to practical use. These are all naturally-occurring IFNα, and they are included in the preferred IFNα of the present invention.

OIF (Otsuka Pharmaceutical Co., BALL-1)

Sumiferon (Sumitomo Pharma Co., NAMALWA)

Wellferon (Glaxo-Wellcome, α-n1)

Alferon (Purdue Frederick Co., α-n3)

BALL-1, NAMALWA, α-n1, and α-n3, which are also shown as origins of the above-described naturally-occurring IFNα, are names of cell lines from which the respective IFNα are derived. "Naturally-occurring" refers to IFNα that is produced by a cell line established from a living body and not prepared by genetic recombination. Naturally-occurring IFNα can be collected from cell culture obtained by culturing cells of the cell lines indicated above as the origins. The methods for culturing cell lines and collecting IFNα from the cultures are known.

Recombinant IFNα is also included in the preferred IFNα of the present invention. Recombinant IFNα refers to IFNα obtained by artificially expressing DNAs encoding the amino acid sequences of IFNα. Furthermore, not only proteins comprising the amino acid sequence of a naturally-occurring IFNα, but also proteins in which the amino acid sequence has been altered can be used as IFNα of the present invention. Specifically, IFNα of the present invention includes, for example, the following proteins:

(a) proteins comprising an amino acid sequence of the naturally-occurring IFNα described above;

(b) proteins comprising an amino acid sequence with substitution, deletion, addition, or insertion of one or multiple amino acid residues in an amino acid sequence of the naturally-occurring IFNα described above, and having the biological activity equivalent to that of the naturally-occurring IFNα;

(c) proteins encoded by a DNA that hybridizes under stringent conditions to the DNA comprising a nucleotide sequence encoding the naturally-occurring IFNα described above, and having the biological activity equivalent to that of the naturally-occurring IFNα; and (d) proteins comprising an amino acid sequence having 90% or higher sequence homology in an amino acid sequence of the naturally-occurring IFNα described above, and having the biological activity equivalent to that of the naturally-occurring IFNα.

In the present invention, the biological activity of naturally occurring IFNα means the capability of the protein to inhibit, improve, alleviate, treat or prevent skin diseases, preferably chronic intractable external otitis, the protein administered by oral administration, oral mucosal application, or gingival application. Whether a certain protein has such an activity can be actually determined, for example, by applying the protein to the gingiva of a test animal.

Such IFNα with an altered amino acid sequence can be called "IFNα variant (modified form)". There are various known methods for altering given amino acid sequences. The amino acid sequence of IFNα can be altered, for example, by introducing mutations into the nucleotide sequence of an IFNα-encoding polynucleotide. The biological activity can be modulated by altering the amino acid sequence. For example, the biological activity of IFNα can be enhanced or its in vivo stability can be improved.

Many methods for altering amino acid sequences are known. Methods described in "Molecular Cloning: A Laboratory Manual" (J. Sambrook, et al., eds., Second Edition, Cold Spring Harbor Laboratory Press, Cold Spring Harbor, N.Y., 1989), "Current Protocols in Molecular Biology" (F. M. Ausubel, et al., eds., John Wiley & Sons, Inc., New York), or other documents can be used, for instance.

Amino acid sequences are altered by substituting, deleting, adding, or inserting amino acid residues. Such substitution, deletion, addition, and insertion of amino acid residues can be done singly, or in combinations of two, three, or all of such modifications. Furthermore, amino acid sequences can be altered by any modifications selected from the group consisting of substitution, deletion, addition, and insertion of amino acid residues at one or multiple positions in the amino acid sequence of naturally-occurring IFNα. Such variants include fusion proteins containing the whole or a partial amino acid sequence of IFNα. There are known methods for predicting the effects of amino acid sequence alterations on protein structure. Thus, variants of IFNα can be designed according to known methods. An example of such methods is described by Dahiyat and Mayo (Science, 1997; 278: 8287). The method of Dahiyat and Mayo can be used to assess whether a structure essential for maintaining the activity remains when the amino acid sequence of IFNα is altered.

Furthermore, it is possible just to alter the amino acid sequence, while the biological activity can be retained. For example, cysteine residues may be substituted or removed to avoid formation of undesired disulfide bonds. Likewise, the protease sensitivity of IFNα can be adjusted by altering the amino acid sequence. Degradation of proteins by proteases in an expression system can be prevented by conferring protease resistance. This allows enhancement of IFNα expression.

When altering the amino acid sequence of IFNα, it is known to be useful to substitute amino acid residues with similar property for retaining the protein structure and activity. Such substitutions of amino acid residues with a similar property are called "conservative substitutions". The "conservative substitutions" refers to amino acid substitutions that do not lead to significant alteration of a protein's tertiary structure and/or activity. For example, substitutions among amino acid residues within each group shown below are included in the conservative substitutions.

(1) neutral hydrophobic side chains (alanine, tryptophan, valine, phenylalanine, proline, methionine, and leucine);

(2) neutral polar side chains (asparagine, glycine, glutamine, cysteine, serine, tyrosine, and threonine);

(3) basic side chains (arginine, histidine, and lysine);

(4) acidic side chains (aspartic acid and glutamic acid);

(5) aliphatic side chains (alanine, isoleucine, glycine, valine, and leucine);

(6) aliphatic hydroxyl side chains (serine and threonine);

(7) amine-containing side chains (asparagine, arginine, glutamine, histidine, and lysine);

(8) aromatic side chain (tyrosine, tryptophan, and phenylalanine); and (9) sulfur-containing side chain (cysteine and methionine).

Various methods known to those skilled in the art can be used for substitution of amino acids. Specifically, the site-directed mutagenesis of Kunkel et al. (Kunkel, Proc. Nat.

Acad. Sci. U.S.A., 1985; 82: 488-492) can be used to substitute amino acids. Alternatively, polynucleotides consisting of the nucleotide sequence encoding a deduced amino acid sequence may be chemically synthesized.

In the present invention, the number of amino acid residues substituted, deleted, added, or inserted is not particularly limited, as long as the resulting variant retains the required biological activity of IFNα. As described above, retention of the biological activity also includes enhancement of the biological activity. The number of amino acid residues to be substituted, deleted, added, or inserted to obtain IFNα variants of the present invention is generally 50 residues or less, for example, 30 residues or less, preferably 20 residues or less, more preferably 10 residues or less, even more preferably 5 residues or less, and still more preferably 1 to 3 residues.

Furthermore, the biological activity of IFNα can be enhanced by altering its amino acid sequence. Species of IFNα with an enhanced biological activity are also included in the IFNα of the present invention. Enhancement of the biological activity includes enhancement of IFNα activity per unit weight, prolongation of retention time in vivo, and suppression of physiological degradation. For example, it has been demonstrated that the biological activity of IFNα can be enhanced by changing the amino acid sequence of IFNα into an amino acid sequence that is conserved among some subtypes (U.S. Pat. Nos. 4,695,623, 4,897,471, and 5,985,265). Such variants can also be used as IFNα of the present invention.

Polynucleotides encoding a variant of IFNα can be obtained through hybridization as well. For example, polynucleotides that hybridize under stringent conditions to a DNA comprising the coding region of a DNA encoding the naturally-occurring IFNα described above are highly likely to encode proteins with the same biological activity as that of IFNα. In the present invention, the "stringent conditions" are specified by parameters known in the technical field. Specifically, conditions of DNA hybridization where the ionic strength is low and the temperature is slightly below the melting temperature (Tm) of DNA hybrid complex are generally defined as stringent conditions. Specifically, conditions where the temperature is about 3° C. lower than Tm are included in the stringent conditions. As the stringency gets higher, the degree of homology between probe and target sequence becomes higher.

For further information on such conditions, one may refer to references summarizing similar methods. Specifically, such methods are described in, for example, "Molecular Cloning: A Laboratory Manual" and "Current Protocols in Molecular Biology" indicated above. By such methods, a DNA encoding the above-described naturally-occurring IFNα can be used as a probe to screen a cDNA library of a species from which IFNα has not been isolated, and isolate IFNα-encoding cDNAs from that species. Alternatively, there is a possibility that novel subtypes of IFNα can be isolated from a cDNA library of a species from which IFNα has already been isolated.

The stringent conditions include, for example, hybridization at 65° C. using 6×SSC. The stringent conditions also include hybridization at 65° C. using a hybridization buffer containing 3.5×SSC, 0.02% Ficoll, 0.02% polyvinylpyrrolidone, 0.02% bovine serum albumin, 2.5 mM $NaH_2PO_4$ [pH 7], 0.5% SDS, and 2 mM EDTA. SSC contains 0.15 M sodium chloride and 0.15 M sodium citrate (pH 7). In the stringent conditions, the DNA-transferred membrane is washed using 2×SSC at room temperature after hybridization, and then washed using 0.1×SSC/0.1×SDS at a temperature up to 68° C.

Alternatively, formamide hybridization solutions may be used instead of an aqueous hybridization solution. Specifically, the stringent hybridization conditions can be achieved, for example, by using 50% formamide solution at 42° C. Those skilled in the art can use other conditions and reagents to achieve comparable stringency. Furthermore, methods of screening cells and libraries for the purpose of expressing variants, methods for isolating such variants, and methods for cloning and sequencing DNAs of interest are also known. For example, primers for amplifying DNAs can be designed based on the nucleotide sequences of the DNAs to be isolated. The DNAs of interest can be amplified by gene amplification methods such as PCR using primers.

In the present invention, the amino acid sequence homology between naturally-occurring IFNα and its variant is in general at least 65%, typically 75%, preferably 90%, more preferably 95% or higher, and still more preferably 99% or higher. The amino acid sequence homology can be calculated using various software tools developed and disclosed by NCBI (Bethesda, Md.). Analytical tools for nucleotide and amino acid sequences include the heuristic algorithm of Altschul S. F., et al. (J. Mol. Biol., 1990; 215: 403-410). This tool is known as BLAST.

In the present invention, IFNα may be modified with other molecules as long as it retains its biological activity. Specifically, fusion proteins between IFNα and other proteins may be used as IFNα of the present invention. Furthermore, IFNα may be modified with non-protein polymers. For example, IFNα modified with polymers such as polyethylene glycol has been used as a preparation administered into the blood (U.S. Pat. Nos. 5,382,657, 5,559,213, 6,177,074, 5,951,974, and 5,981,709). Such modifications with polymers can improve the retention of IFNα in the blood.

IFNα used in the present invention can be synthesized chemically or by genetic engineering based on its amino acid sequence. Alternatively, naturally-occurring IFNα may be used in the present invention. Naturally-occurring IFNα can be extracted from organisms or biological materials. Alternatively, naturally-occurring IFNα can also be collected from cultures obtained by culturing IFNα-producing cells. Of such methods, the synthesis method by genetic engineering is a preferred method for obtaining homogeneous IFNα on a large scale easily. When the amino acid sequences to be synthesized are known, those skilled in the art can predict the encoding nucleotide sequences and synthesize them. Alternatively, those skilled in the art can prepare cDNA for naturally-occurring IFNα or its variants and translate them into proteins. There are many known methods of in vivo or in vitro protein translation based on amino acid sequence-encoding DNAs. For example, to translate proteins in vivo, in general, 5'-untranscribed and 5'-untranslated sequences, which are involved in transcription and translation initiations, respectively, and the like can be combined, if required. More specifically, a promoter sequence for regulating gene transcription can be linked to a gene as a 5'-untranscribed regulatory sequence. An enhancer can also be added as a transcribed regulatory sequence.

Expression vectors containing all the elements necessary for expression are available on the market. Known vectors are also described, for example, in "Molecular Cloning: A Laboratory Manual" (Sambrook, et al., Second Edition, Cold Spring Harbor Laboratory Press, 1989). In general, such commercially available vectors are equipped with multi-cloning sites for inserting amino acid sequence-encoding DNAs. Expression vectors can be prepared by digesting the DNA to be expressed with appropriate restriction enzymes and inserting it into a cloning site. Restriction enzyme sites that are needed can also be prepared by ligation with synthetic oligonucleotides. IFNα can be expressed as a fusion protein by using fusion protein-expression vectors. For example, vectors that can be attached with a myc or His tag or such are also known.

The expression vectors thus prepared are introduced into and transform host cells that allow translation of proteins of interest. Such host cells include, for example, the following cells:

prokaryotic cells (for example, *E. coli*); and eukaryotic cells (for example, CHO cell, COS cell, yeast expression system, and insect cells).

When the IFNα to be used in the present invention is predicted to contain glycosylation sites, eukaryotic cells are preferably used as host cells. For example, at least three glycosylation sites are predicted in the amino acid sequence of canine IFNα obtained using the baculovirus expression system (see Japanese Patent No. 5046030). Eukaryotic cells can be used for such IFNα expression.

The eukaryotic cell expression systems include, for example, insect cells. Methods for expressing foreign DNAs in insect cells using the baculovirus expression system are known. Foreign DNAs can be expressed in insect cells, for example, by the method described in Japanese Patent No. 5046030.

Since naturally-occurring IFNα is secretory proteins, signal sequences are generally encoded in the IFNα-encoding cDNAs derived from a living body. For example, the N-terminal 23 residues of the canine IFNα shown in SEQ ID NO: 2 correspond to a signal sequence.

When the IFNα to be used in the present invention is synthesized by genetic engineering techniques as described above, a foreign signal sequence may be used as the signal sequence. For example, when human IFNα is expressed in nonhuman cells, a functional signal sequence in the species from which the cells used for the actual expression have been derived can be used. In this case, a chimeric protein is expressed, in which a signal sequence that is functional in the nonhuman species is attached to the amino acid sequence of a mature human IFNα protein. The signal sequence is removed during the process of secretion of the expressed recombinant protein to the outside of cells. As a result, the mature human protein is secreted. Alternatively, when it is not necessary to secrete the protein to the extracellular space, a DNA encoding the amino acid sequence of the mature protein can also be expressed. When the deletion of the signal sequence results in loss of the start codon, a start codon (atg) can be artificially added to the 5' end.

When the amino acid sequence containing a signal sequence is expressed, IFNα is accumulated in the culture supernatant. Alternatively, when the amino acid sequence does not have a signal sequence and is expressed, the mature IFNα protein is accumulated in the cells. After collection and purification from the culture, suchα expressed by gene recombination can be used for the composition of the present invention. Methods for collecting and purifying IFNα from cultures are known. Alternatively, cultures containing the expression product or crude preparation can be used for the composition of the present invention. For example, IFNα expressed using yeast as the host can be freeze-dried without removing the yeast cells, and formulated into the composition of the present invention.

Further, the IFNα to be formulated into the composition of the present invention may be expressed using a plant as host (for example, strawberry). In this case, plants or plant cells of a transformed plant that express IFNα can be used as raw materials for the composition of the present invention. The present invention provides the composition for preventing and/or treating chronic intractable external otitis, comprising a transformed plant containing an IFNα-encoding gene in an expressible manner. Alternatively, the present invention relates to a composition for preventing and/or treating chronic intractable external otitis, the composition comprising an IFNα-containing fraction derived from a transgenic plant retaining the gene encoding IFNα so as to be expressible.

For example, IFNα-containing tissues of a transformed plant may be destroyed and formulated into the composition of the present invention. Such plant tissues can be crushed after drying. Alternatively, crushed plant tissues may be dried. Alternatively, IFNα-containing tissues of a transformed plant are homogenized, and filtered if required, and the resulting IFNα-containing solution can be formulated into the composition of the present invention without further treatment or after being dried. Such IFNα-containing fractions derived from transformed plants are all included in the "transformed plants" of the present invention.

The composition on gingiva of the present invention can be produced without making significant changes in current manufacturing processes, by using the same plants as currently used as materials for feed or pet food as transformed plants.

Specifically, such plants include strawberry, potato, tomato, beans, cereals, fruits, and pasture grasses. Beans include soybeans and azuki-beans. Cereals may include rice plant, wheat, and corn.

The transformed plant cells used in the present invention can be prepared by introducing a vector carrying an IFNα-encoding gene (or a protein having a biological activity equivalent to IFNα) into plant cells, and expressing the gene. A known endoplasmic reticulum retention signal (e.g., KDEL (SEQ ID NO: 5) or RDEL (SEQ ID NO: 6)) can also be added to the C terminal of IFNα for the expression of IFNα in plant cells. The endoplasmic reticulum retention signal comprises, for example, the following amino acid sequence. Secretory proteins with an endoplasmic reticulum retention signal are stably maintained in the endoplasmic reticulum after expression.

Specifically, the present invention provides the composition for oral administration, oral mucosal application or gingival application for preventing and/or treating chronic intractable external otitis, which comprise a transformed plant carrying in an expressible manner an IFNα-encoding gene with an endoplasmic reticulum retention signal attached to its C terminus. Alternatively, the present invention relates to the composition for oral administration, oral mucosal application or gingival application for preventing and/or treating chronic intractable external otitis which comprise a fraction containing IFNα derived from a transformed plant carrying in an expressible manner an IFNα-encoding gene with an endoplasmic reticulum retention signal attached to its C terminus.

Vectors used for gene expression in plant cells are not particularly limited, as long as they contain a promoter that allows transcription in the plant cells and a terminator sequence containing a polyadenylation site required for the stabilization of transcripts. Vectors that can be used include, for example, the "pBI121", "pBI221", and "pB1101" plasmids (all from Clontech). The promoters that allow transcription in plant cells include, for example, promoters that allow constitutive gene expression in plant cells and promoters that are inducibly activated upon foreign stimulation. Known promoters that allow constitutive expression include the following promoters:

cauliflower mosaic virus 35S promoter (Odell et al., Nature, 1985; 313: 810);

rice plant actin promoter (Zhang et al., Plant Cell, 1991; 3: 1155); and maize ubiquitin promoter (Cornejo et al., Plant Mol. Biol., 1993; 23: 567).

IFNα can be expressed in plant cells by introducing plant cells with a vector carrying an IFNα-encoding gene operably linked to such a promoter. Herein, "operably linked" means that a promoter is linked to an IFNα-encoding gene so that IFNα is expressed in plant cells. "Plant cells" to be transformed include various types of plant cells. Transformants can be prepared by introducing vectors into, for example, suspension culture cells, protoplasts, leaf pieces, or calluses.

Methods for introducing vectors into such plant cells are known. Specifically, various methods known to those skilled in the art can be used, including *Agrobacterium*-mediated methods, polyethylene glycol methods, electroporation, and particle gun methods.

Plants can be regenerated by re-differentiating the transformed plant cells. Re-differentiation methods, which vary depending on the plant species, have already been established. Methods for re-differentiating each plant species are listed below.

Potato: Method of Visser et al. (Theor. Appl. Genet, 78: 594 (1989)); Tuber disc methods.

Monocotyledonous Cereals Such as Rice Plant: Method of Hiei et al. (Hiei, Y., Komari, T., Kubo, T. Transformation of rice mediated by *Agrobacterium tumefaciens*. Plant Mol. Biol., 1997; 35: 1-2 205-18); Method of Ishida et al. (Ishida, Y., Saito, H., Ohta, S., Hiei, Y., Komari T., Kumashiro T. High efficiency transformation of maize (*Zea mays* L.) mediated by *Agrobacterium tumefaciens*. Nat. Biotechnol., 1996 June; 14: 6 745-50); Electroporation (Shimamoto, K., Terada, R., Izawa, T. et al. Fertile transgenic rice plants regenerated from transformed protoplasts. Nature, 338, 274-276 (1989)); etc.

Strawberry: Method of Asao et al. (Asao, H., Y. Nishizawa, S. Arai, T. Sato, M. Hirai, K. Yoshida, A. Shinmyo and T. Hibi. Enhanced resistance against a fungal pathogen *Sphaerotheca humuli* in transgenic strawberry expressing a rice chitinase gene. Plant Biotechnology, 14 (3): 145-149 (1987)).

Once a transformed plant with an IFNα-encoding gene introduced into its genome (chromosome) is generated, progeny can be obtained from the plant via sexual or asexual reproduction. Alternatively, the plant can be produced on a large scale from breeding materials obtained from the plant and its progeny, or their clones. The breeding materials include, for example, seeds, fruits, cut panicles, tubers, tuberous roots, strains, calluses, and protoplasts.

Furthermore, techniques using plant virus vectors for expressing proteins of interest in plants are known. When plant virus vectors that do not integrate into the genome are used, foreign genes are generally not transferred to progeny. So far, however, the expression level of a foreign gene expressed using a plant virus vector is known to be higher than that achieved by a chromosome integration method such as the *Agrobacterium*-mediated method. The tobacco mosaic virus vector is a known practicable plant virus vector. Specifically, substances of interest can be produced in plants by growing the plants and inoculating them with infectious RNA transcribed from a constructed expression gene during the inoculable period.

The composition of the present invention is useful for prevention and/or treatment of chronic intractable external otitis in mammals. In the present invention, prevention means inhibiting the progression of chronic intractable external otitis. In a state where no symptoms appear, prevention means delaying the occurrence of symptoms. Treatment of chronic intractable external otitis means alleviating at least one symptom of the disease. In the present invention, symptoms of chronic intractable external otitis to be prevented or treated include localized or diffuse otitis externa, eczema of external auditory canal, and fungal otitis externa (e.g., Malassezia external otitis).

Mammals to which the composition of the present invention is administered preferably are humans, pet animals such as dogs and cats, and mammals kept in zoos. Such mammals include pigs, boars, goats, sheep, horses, cattle, deer, donkeys, reindeer, rabbits, monkeys, gorillas, orangutans, chimpanzees, bradypods, elephants, giraffes, rhinoceroses, hippopotamuses, tapirs, wolves, hyenas, bears, pandas, lesser pandas, masked palm civets, foxes, raccoon dogs, raccoons, tigers, lions, leopards, cheetahs, otters, seals, fur seals, Steller's sea lions, sea lions, dolphins, killer whales, and whales. Preferred are dogs.

In the present invention, the composition of the present invention refers to a composition for oral administration, oral mucosal application or gingival application to a mammal. As used herein, "oral mucosa" means any mucosal surfaces accessible by administration to oral cavity which are found in an oral cavity, for example, without limitation, (i) found on a tongue surface, i.e., mucosa on a tongue surface; (ii) on a sublingual surface, i.e., mucosa lining oral cavity bottom; (iii) on a buccal surface, i.e., mucosa lining bucca; (iv) on a palatal surface, i.e., mucosa lining palatal; (v) on a pharyngeal surface, i.e., mucosa lining pharynx; (vi) on a gingival surface, i.e., gingival mucosa; and (vii) on a gingival sulcus, i.e., cavity formed between teeth and gums.

The composition of the present invention can be produced by mixing interferon-α and a biologically acceptable carrier. The biologically acceptable carrier includes carriers that are inert to interferon-α to be compounded and an organism to which the composition is administered. A carrier inert to an organism means that the carrier does not interfere with normal biological functions. Normal biological functions include metabolic function, reproductive function, motor function, and neural action. For example, components which are metabolized by the normal metabolic function of an organism are included in a biologically acceptable carrier. Alternatively, components which are not or hardly digested or metabolized and do not interfere with biological functions are all included in a biologically acceptable carrier. For example, a food compound containing IFNα constitutes a preferred aspect of the composition of the present invention. The composition of the present invention can also be orally administered as a pharmaceutical composition for the prevention or treatment of chronic intractable external otitis.

In other words, the present invention relates to a pharmaceutical composition for preventing and/or treating chronic intractable external otitis, the pharmaceutical composition comprising interferon-α as an active ingredient. Alternatively, the present invention relates to a pharmaceutical composition for preventing and/or treating chronic intractable external otitis, the pharmaceutical composition comprising interferon-α and a pharmaceutically acceptable carrier. The invention further relates to the use of interferon-$\alpha$ in manufacturing a pharmaceutical composition for preventing and/or treating chronic intractable external otitis. The present invention also relates to the use of interferon-$\alpha$ in a method for preventing and/or treating chronic intractable external otitis.

In particular, in the prior art, an active treatment method against chronic intractable external otitis has not been known. In the present invention, as confirmed also in Example 7, a therapeutic effect on an already-advanced chronic intractable external otitis was confirmed by administering the therapeutic agent for chronic intractable external otitis of the present invention. In other words, the present invention provides a therapeutic agent for chronic intractable external otitis, the therapeutic agent comprising interferon-$\alpha$ as an active ingredient. Alternatively, the present invention relates to a pharmaceutical composition for treating chronic intractable external otitis, the pharmaceutical composition comprising interferon-$\alpha$ and a pharmaceutically acceptable carrier. The invention further relates to the use of interferon-$\alpha$ in manufacturing a pharmaceutical composition for treating chronic intractable external otitis. The present invention also relates to the use of interferon-$\alpha$ in the treatment of chronic intractable external otitis.

Next, specific embodiments of the composition of the present invention, which comprise interferon$\alpha$, are described below.

Food Composition Containing Interferon$\alpha$:

In general, the composition of the present invention can be prepared by formulating interferon$\alpha$ into an ingredient ingested as food or feed for mammals. In particular, when feed is given to pet animals, it is called pet food. Pet food is included in the food or feed of the present invention. “Pet animals” refers to nonhuman animals bred for ornamental and sporting purposes. Animals bred, for example, as working animals or for animal products such as meat, eggs, hair, milk, and such are in general included in farm animals, and distinguished from pet animals. However, some animals bred to perform specific tasks (working animals) such as police dogs and guide dogs may consume the same type of feed as sporting animals. Even if some animals are bred as working animals, as long as they are of the same species as pet animals and consume the same type of feed as pet animals, their feed is included in the pet food defined in the present invention.

In general, food and feed contain carbohydrates, proteins, minerals, fats, water, fibers, and the like, and most of the materials are animal or plant tissues, microorganism cells, and their processed products. “Processed products” refers to products yielded from such materials via some processes such as heating, drying, freeze-drying, and extraction. A series of processes for obtaining a processed product may contain a combination of several different steps.

Food and feed may be formulated with preservatives, antiseptic agents, antioxidants, dyes, flavors, humectants, seasonings, and such. Components such as expanders, binders, and viscosity adjusters can be added depending on the type of food, and naturally-occurring or synthetic components are used. Food composition of the present invention can be produced by formulating IFN$\alpha$ into materials commonly used for food or feed. Alternatively, the oral composition of the present invention can be prepared by adding IFN$\alpha$ to IFN$\alpha$-free food or feed at the time of ingestion. Next, specific examples of the composition of the present invention are described below.

Food or feed composition of the present invention can be prepared by adding interferon$\alpha$ to materials generally used as food or feed. The amount of interferon-$\alpha$ added to the food composition or feed composition according to the present invention is usually 1 to 15,000 LU/day/kg of body weight, preferably 0.5 to 25,000 LU/day/kg of body weight. In other words, 1 to 15,000 LU, preferably 0.5 to 25,000 LU/kg of body weight of interferon-$\alpha$ can be compounded for a standard food or feed intake per day. When the food composition is a nonessential food such as chewing gum, the dosage of interferons can be controlled by indicating the daily amount of the food to be ingested according to its blending quantity of interferon. For example, when the blending quantity in a single piece of chewing gum corresponds to the daily dose, the recommended amount of the chewing gum to be ingested is a single piece per day.

Chewable Composition Containing Interferons:

The IFN$\alpha$-containing composition of the present invention can be prepared as a chewable oral composition by combining IFN$\alpha$ with chewable carriers. Specifically, the present invention provides the composition containing IFN$\alpha$ and chewable carriers. In the present invention, “chewable carrier” refers to components that are masticated when administered to the oral cavity of an animal. Such chewable carriers may be materials that are hard to crush or materials that can be crushed into pieces by mastication. Specifically, chewable carriers include, for example, glucose, sucrose, maltose, sorbitol, xylitol, trehalose, starch, gelatin, alginic acid, alginate, cellulose, ethylcellulose, carboxymethylcellulose, hydroxypropylcellulose, hydroxypropylmethylcellulose, guar gum (polygalactomannan), glucomannan, xanthan gum, and Carbopol.

Alternatively, various gum bases are also included in the chewable carriers of the present invention. Carriers whose volumes remain constant even after being chewed for a long time in the mouth are in general used as gum bases. Gum bases include, for example, plant resins, chicle, vinyl acetate resins, ester gum, polyisobutylene, calcium carbonate, and jelutong (Pontianak). When the chewable composition of the present invention is processed as an oral composition for human, gum bases are particularly preferred as chewable carriers.

When the chewable composition of the present invention is used as pharmaceuticals, they are a chewable pharmaceutical composition. When the chewable composition of the present invention is provided as food, they are chewable food. When the composition of the present invention is used as chewable feed, it is a chewable feed composition. The size of a chewable composition can be adjusted to induce mastication in nonhuman animals. Specifically, mastication can be induced in nonhuman animals by processing the composition to be bulkier than an easy-to-swallow size. More frequent mastication can also be induced by increasing the hardness depending on the type of animal.

Paste-Type Composition Containing Interferon$\alpha$:

The IFN$\alpha$-containing composition of the present invention can also be prepared as paste-type composition by combining IFN$\alpha$ with paste carriers. Specifically, the present invention provides the composition containing IFN$\alpha$ and paste carriers. In the present invention, the paste carrier may also be referred to as a carrier with semisolid consistency. Alternatively, the paste carriers also include gel carriers.

Paste-type composition can be prepared, for example, by adding a solvent such as water to water-soluble polysaccharides or polymers. The water-soluble polysaccharides and polymers include glucose, sucrose, maltose, sorbitol, xylitol, starch, gelatin, pectin, alginic acid, alginate, cellulose, ethylcellulose, carboxymethylcellulose, hydroxypropylcellulose, hydroxypropylmethylcellulose, guar gum (polygalactomannan), glucomannan, carrageenan, xanthan gum, tamarind gum, Carbopol, agarose, and agar. In addition to these, polymers such as polyethylene glycol and polyvinylpyrrolidone can be formulated as gel carriers into the composition of the present invention.

The composition of the present invention can be in any form of choice such as solid, gel, or liquid. In order to maintain IFNα activity, the composition is preferably in a dried form when they are distributed on the market. The dried composition can be converted into gel or liquid by adding an appropriate solvent such as water to the composition at the time of ingestion. The composition of the present invention may also be distributed on the market in a freeze-dried form.

The composition of the present invention may contain additional components such as flavors, dyes, corrigents, sweeteners, and seasonings. The toothbrushing effect can also be achieved by further formulating plant fibers or such into the composition formulated with chewable carriers.

The content of IFNα which can be contained in the composition of the present invention is usually 0.5 to 25,000 LU/day/kg of body weight, for example, 1 to 15,000 LU/day/kg of body weight, more specifically 2 to 5,000 LU/day/kg of body weight, usually 2 to 500 LU/day/kg of body weight, preferably about 2 to 10 LU/day/kg of body weight. For example, the dosage of IFNα administered in anticipation of antiviral effect in blood is as high as several MIU to 10 MIU (1 MIU=1000 IU). In contrast, by keeping the amount of IFNα used low, the risk of side effects caused by IFNα administration in the present invention is negligibly small. The mixing ratio of IFNα in the composition of the present invention can be determined based on the intake of the composition. For example, when mixed in a feed, the amount of IFNα to be mixed to the feed can be determined based on the body weight of the animal to which the composition of the present invention is to be administered and the intake amount of the feed per day. Note that 1 LU in the present invention corresponds to 1 IU of human native IFNα.

Alternatively, instructions can be given to explain that the daily amount (g) of composition of the present invention to be ingested per kilogram of body weight is based on the blending quantity of IFNα in the composition. In other words, the present invention provides a kit for preventing and/or treating chronic intractable external otitis, the kit comprising:

(1) a composition comprising interferon-α and a biologically acceptable carrier; and (2) an instruction describing the effective dose for preventing and/or treating chronic intractable external otitis of the composition.

In the present invention, potency (LU) of IFNα can be determined according to, for example, the method described in Japanese Patent No. 5046030.

The composition of the present invention can be applied to animals (for example, by oral administration or oral mucosal or gingival application) to realize the effect of preventing and/or treating chronic intractable external otitis. In other words, the present invention provides a method for preventing and/or treating chronic intractable external otitis in a mammal, the method comprising a step of applying interferon-α. In particular, a method of treating chronic intractable external otitis comprising a step of applying interferon-α to gingivae of mammals, preferably dogs, is a preferred aspect of the present invention.

The composition of the present invention can be applied to gingivae of mammals in any form such as in a solid, paste, gel, or liquid form. Solid preparations can be applied to gingivae indirectly via chewing or swallowing. Alternatively, solid preparations can be indirectly applied to gingivae as a lozenge (so-called troche). Paste or gel preparations can be applied to gingivae directly as well as via chewing or swallowing. Liquid preparations can be administered via spraying on gingivae, mouth washing or gargling as well as via swallowing.

When the present invention is applied as a medical practice, the composition of the present invention is used as a pharmaceutical composition. In other words, the present invention provides a pharmaceutical composition for preventing and/or treating chronic intractable external otitis in mammals, the pharmaceutical composition comprising interferon-α and a pharmaceutically acceptable carrier. In the present invention, as the pharmaceutically acceptable carrier, inert carriers used for drug formulation can be usually used.

The present invention will be described below in more detail based on the Examples.

All prior art documents cited herein are incorporated herein by reference.

EXAMPLES

[Example 1] Cloning of Canine Interferon-α (CaIFNα-4) Gene

CaIFNα4 gene was cloned by PCR from a cDNA library prepared from mRNA of canine cells (MDCK cells) as a template stimulated by Newcastle disease virus B1 strain inactivated with ultraviolet light. The sequences of the primers used for the cloning are as follows.

```
Sense primer:
                                        (SEQ ID NO: 3)
5'-GCAGGATCCACGATGGCCCTGC-3';
and

Antisense primer:
                                        (SEQ ID NO: 4)
5'-GCTGAGCTCAAAGTTCATCCTTATGATGATGATGATGATGTTTCCTC
CTCCTTACTCTT-3'
```

For the CaIFNα-4 gene (SEQ ID NO: 1; amino acid sequence: SEQ ID NO: 2), a BamHI sequence was added to the 5' end side and a SacI sequence was added to the 3' end side by PCR. Furthermore, for the purpose of affinity purification of the expressed protein and for the purpose of inhibiting the secretion of the expressed protein from the endoplasmic reticulum and allowing it to accumulate in the host cell, a His-Tag sequence and an endoplasmic reticulum retention signal KDEL were added downstream of the CaIFNα-4 sequence, respectively. DNA fragments (hereinafter referred to as CaIFNα-4-His-KDEL) amplified by PCR were introduced into a pCR 2.1 vector (Invitrogen) by TA cloning method, transformed into *E. coli*, and cloned. Plasmids were extracted from the *E. coli* transformant and the nucleotide sequence was determined.

[Example 2] Preparation of Canine Interferon-α (CaIFNα-4) Gene for Expression in Plants After confirming the nucleotide sequence, the plasmid was co-digested with restriction enzymes BamHI and SacI to excise the CaIFNα-4-His-KDEL gene (BamHI-SacI fragment). A plant expression vector pBE2113-GUS (Plant Cell Physiol. 1996, 37, 49-59) was co-digested with the same restriction enzymes BamHI and SacI and subjected to CIAP treatment, and then mixed and ligated with the CaIFNα-4-His-KDEL gene (BamHI-SacI fragment) to prepare pBE2113-CaIFNα-4-His-KDEL.

[Example 3] Strawberry Transformation

Strawberry transformation experiments were carried out by introducing pBE2113-CaIFNα-4-His-KDEL into *Agrobacterium* (Rhizobium radiobacter LBA 4404) and selecting kanamycin (Km) resistant strains. Callus induction and redifferentiation were carried out using Km-supplemented medium, and Km-resistant individuals were selected. Introduction of CaIFNα-4 gene was confirmed by Genomic PCR method using DNA extracted from leaves of the Km resistant individual as a template (FIG. 1).

[Example 4] Cultivation and Fruit Collection of CaIFNα-4 Expressing Transgenic Strawberry Strawberry culture seedlings of high expression strains in which expression of the target protein was confirmed were conditioned and hydroponically cultivated, and fruit was collected.

[Example 5] Evaluation of Physiological Activity of CaIFNα-4 Expressed in Transgenic Strawberry (Fruit)

Baculovirus-expressed CaIFNα-4 was prepared as a positive control and a standard for evaluation of CaIFNα physiological activity, according to Japanese PCT Patent Application Re-laid-open No. 2007-080942 (Japanese Patent Application No. 2007-553936). Harvested CaIFNα-4 transgenic strawberry fruit was crushed with PBS to prepare a fruit homogenate. A non-transgenic strawberry fruit homogenate was prepared as a negative control. Evaluation of the physiological activity was carried out by cytopathic effect (CPE) inhibition assay using pig Vesicular Somatitis Virus (VSV) which is a general assay for the biological activity of interferon-α. Canine-derived A-72 cells were used as susceptible cells. For the potency assay of CaIFNα-4, a homogenate, a positive control and a negative control diluted $10^4$ to $128\times10^4$ fold in two steps in the maintenance medium were tested as samples. The test method is described in detail below. Note that as used herein the antiviral activity of interferon-α is represented by the unit "LU", and the unit "LU" and the international unit "IU" illustrating the activity of interferon-α are synonymous in antiviral activity.

Figure 2:
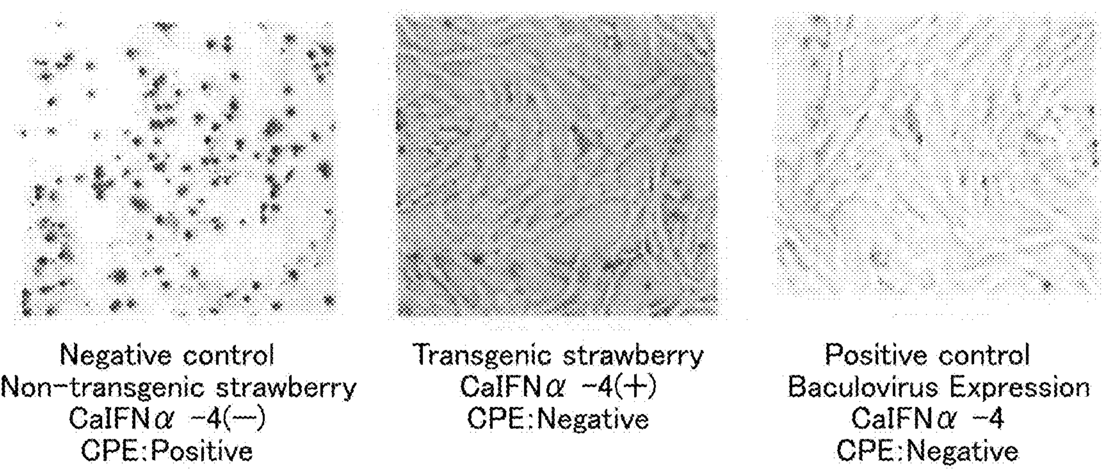
FIG. 2 illustrates results of examining cytopathic inhibitory effect and antiviral activity using fruit homogenates of CaIFNα-4 transgenic strawberries.

Five milliliters of A-72 cell suspension prepared at $1\times10^5$/ml was added to a 25 ml flask and cultured at 37° C. and 5% $CO_2$ for 2 days. When the A-72 cells formed a monolayer, the medium in the flask was removed, and 5 ml of each of the strawberry homogenates diluted $10^3$-fold with a maintenance medium was added. The cells were cultured at 37° C. and 5% $CO_2$ for 1 day, and 0.5 ml of the VSV diluent prepared at 1,000 MOI with a maintenance medium was added. After being cultured at 37° C. and $CO_2$ for 3 days, the cells in the flask were observed under an inverted microscope. FIG. 2 illustrates results of examining cytopathic inhibitory effect and antiviral activity using fruit homogenate of CaIFNα-4 transgenic strawberry. Further, each 100 μl of A-72 cell suspensions prepared at $1\times10^5$ cells/ml with a growth medium was added to each well of a 96-well microplate and cultured at 37° C. and 5% $CO_2$ for 2 days. When the A-72 cells formed a monolayer, the medium was removed from each well and samples and standard samples (prepared by 2-fold serial dilution of baculovirus-expressed CaIFNα-4 prepared at $1.0\times10^4$ LU/ml to $0.5\times10^4$ to $64\times10^4$ times) were added to 4 wells per sample. To cell control wells and virus control wells, 100 μl of maintenance medium was added. The cells were cultured at 37° C. and 5% $CO_2$ for 1 day, and each 10 μl/well of VSV diluents prepared at $1.0\times10^3$ MOI with a maintenance medium was added to each sample well and virus control well. After culturing the cells at 37° C. and 5% $CO_2$ for 3 days, the medium on the plate was removed, 80 μl of 1% crystal violet stain solution was added to each well, and the plate was allowed to stand in the dark at room temperature for 30 minutes. After washing with flowing water and air-drying, the absorbance at a wavelength of 595 nm was measured using a plate reader, and it was confirmed that CaIFNα-4 expressed in transgenic strawberry fruit had the biological activity (antiviral activity) and was quantifiable.

For the potency assay of CaIFNα-4-expressing strawberry fruit homogenate, according to "Use of Getah virus for antiviral assay of human interferon" (Virus 55 (2) 317-326 (2005)), the measurement method using Getah virus with higher safety was investigated. Since a high correlation was found between the results of CaIFNα-4 potency assay with VSV and with Getah virus (Haruna strain) (r2=0.99686), Getah virus was used.

[Example 6] Preparation of Test Drug

The harvested CaIFNα-4-expressing strawberry fruit was lyophilized and crushed to prepare a lyophilized powder. The lyophilized powder of CaIFNα-4-expressing strawberry was mixed with maltose as a stabilizer to prepare a test drug. The potency assay of the test drug was performed to confirm that the potency was $1.2\times10^4$ LU/g.

[Example 7] Administration Test (First)

The test drug prepared in the above Example 6 was administered to a test dog and the anti-inflammatory effect against Malassezia external otitis was examined. Six Shibas aged six months old were prepared as test dogs, and experimental infection of Malassezia was carried out as follows.

Malassezia pachydermatis (ATCC 14522 strain) was used as Malassezia. The lyophilized microbial cells were dissolved in sterile distilled water and cultured on Sabouraud agar at 30° C. for 7 days. Colonies in which development was observed were sufficiently scraped off, suspended in sterile physiological saline, and used as a stock solution. Part of the stock solution was serially diluted 10-fold, and 10 μL aliquots were taken from each diluted bacterial solution. The number of bacteria in the aliquot was counted. The bacterial number multiplied by the dilution ratio was defined as the number of bacteria in the stock solution. The aliquot was diluted with sterilized physiological saline so as to be $1.7\times10^6$/0.1 mL to prepare a bacterial solution for challenge. Each 0.1 mL of the prepared challenge bacterial solutions was inoculated into the left and right external ears of all six dogs to be tested so that the dogs were experimentally infected.

The test dogs after the experimental infection were observed to examine whether four symptoms of pruritus, redness in external ear, bad odor of external ear, dark brown coloring of cerumen characteristic of Malassezia external otitis were developed. The onset of each symptom was scored 1 and the symptoms were scored. In other words, the score was zero when there was no onset of the symptoms, and was a maximum score of 4 when all four symptoms were observed (for example, when pruritus and cerumen were confirmed as symptoms, the score was 2).

On the 7th day after challenge with the bacterial solution, three dogs were divided into two groups, to which a test drug treated group and a non-administration control group were assigned. The body weights of the test dogs at the time of administration are illustrated in Table 1.

TABLE 1

| Study group | No | Body weight (Kg) |
| --- | --- | --- |
| Control group | C1 (No. 13) | 4.5 |
| | C2 (No. 14) | 4.4 |
| | C3 (No. 18) | 5.1 |
| Treated group | T1 (No. 15) | 4.5 |
| | T2 (No. 16) | 4.3 |
| | T3 (No. 17) | 4.0 |

The method of administration was oral, more specifically carried out as follows.

CaIFNα-4 as a test drug equivalent to 2500 LU (about 0.2 g) was weighed, and a small amount of water (100 μl or less) was dropped thereto and kneaded to form a paste. The whole amount of the pasty test drug was applied to the gingivae of the test dogs.

Figure 3:
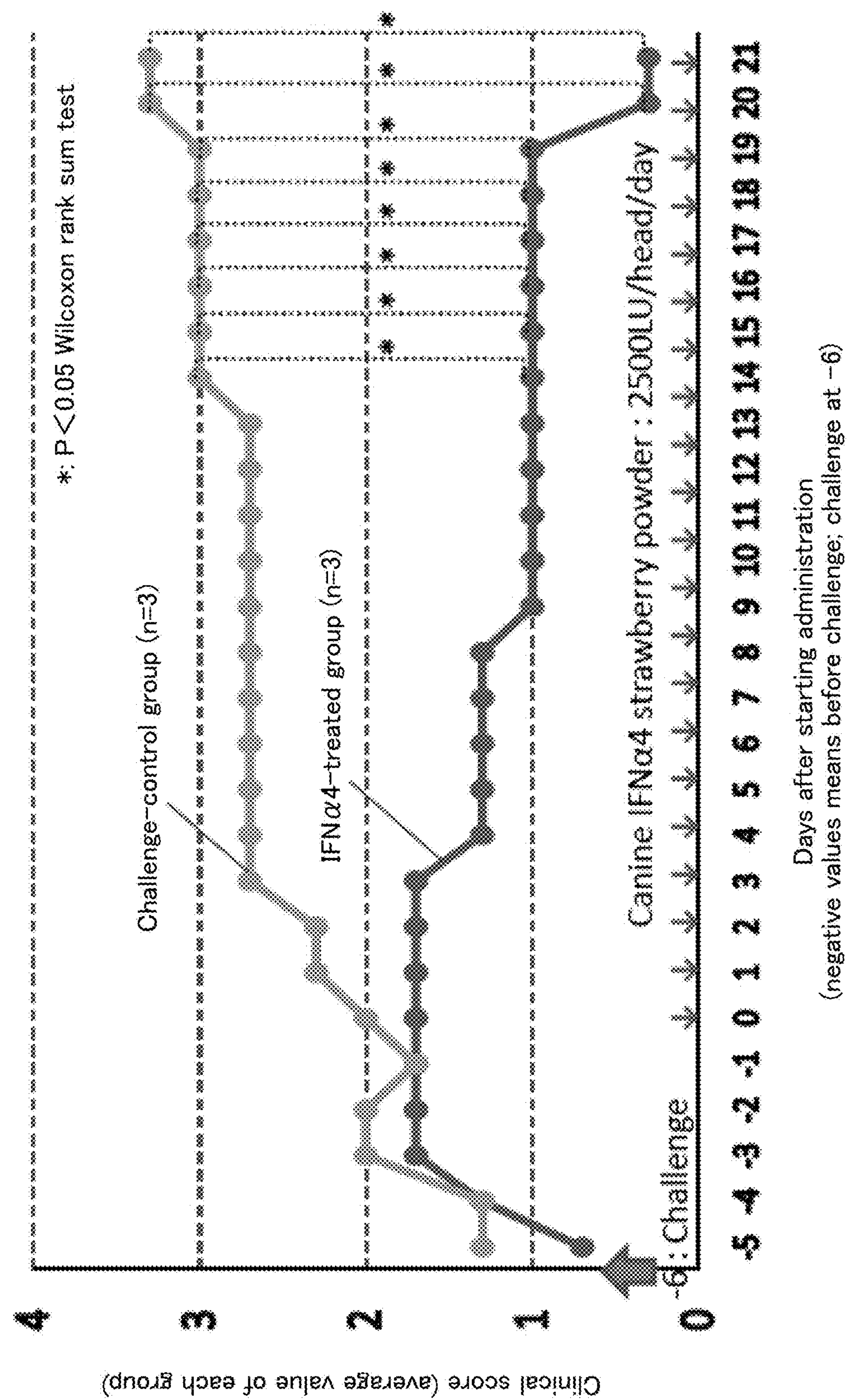
FIG. 3 illustrates transitions of clinical findings for external ears of each group during administration period. IFNα-4 at 2,500 LU/head/day was applied onto gingivae of three test dogs in a treated group daily for 21 consecutive days before feeding. Observation findings for the external ear were recorded in comparison with three dogs in a non-treated group.

Onto the gingiva of three test dogs in the treated group, 2,500 LU/head/day was applied daily for 21 consecutive days before feeding. Observation findings for the external ear were recorded in comparison with three dogs in the non-treated group. FIG. 3 illustrates transitions of the clinical findings for external ears of each group during administration period. The onset of gingival application of the test drug in the treated group resulted in significant alleviation in the symptoms compared to the non-administration control group. A recovery tendency was observed from the 9th day after the start of administration, and the difference in clinical score on the 14th day after the start of administration was significant as compared with the non-treated group.

Figure 4:
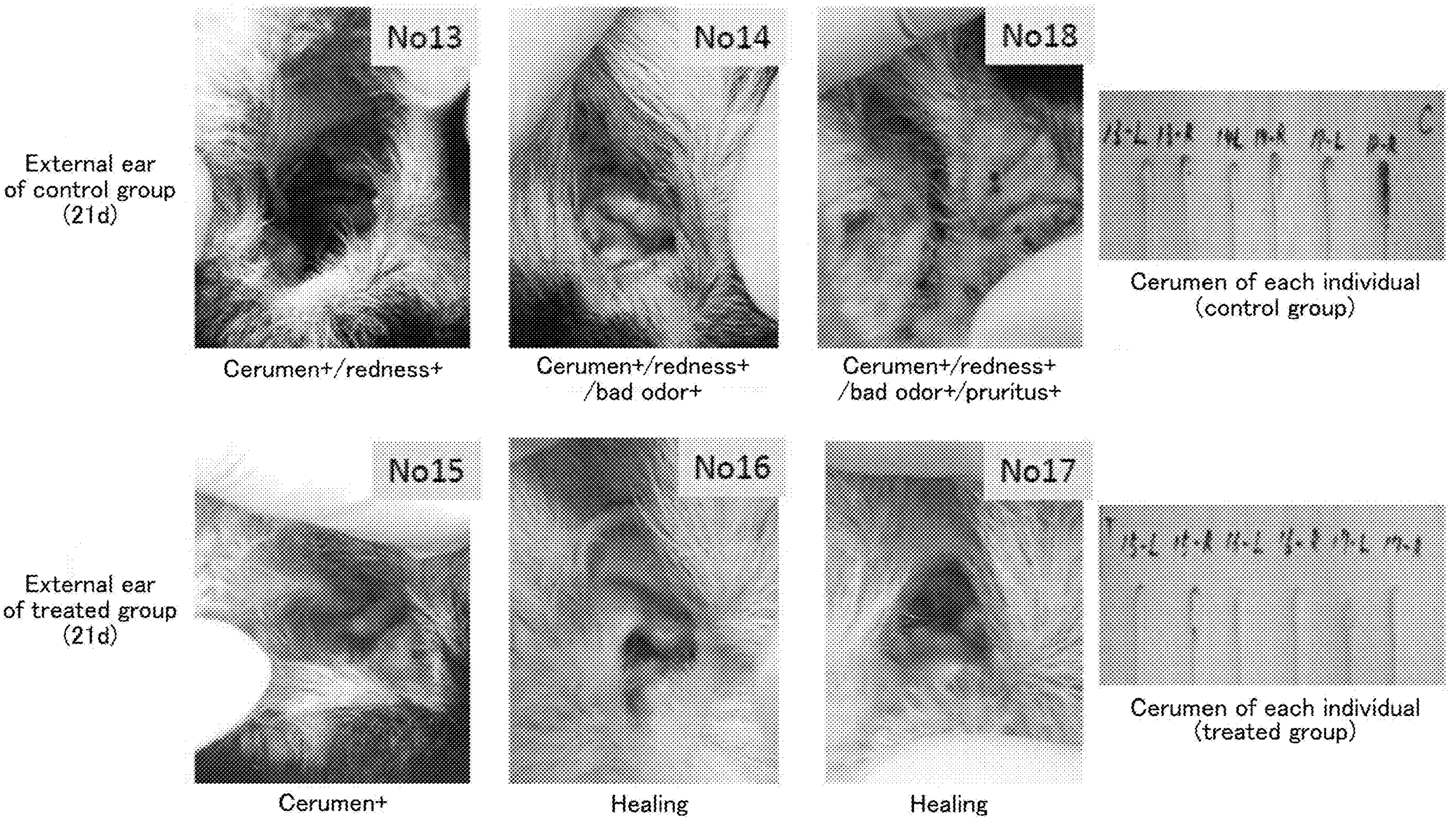
FIG. 4 illustrates photographs depicting findings for external ears and degree of cerumen browning in each test dog on the 21st day after the start of administration.

FIG. 4 illustrates photographs depicting findings for external ears and degree of brown color of cerumen of each test dog on the 21st day after the start of administration. Local lesions in the external ear in the treated group were found to be clearly reduced. During the administration period of the test drug, no adverse reactions or the like which are considered to be caused by administration of this drug was observed in all the individuals of the treated group.

From the above, it was revealed that administration of canine interferon-α via gingiva application illustrated an anti-inflammatory effect on intractable external otitis caused by Malassezia species.

[Example 8] Administration Test (Second)

The administration test is based on the method described in Example 7, except that the test drug in which the content of CaIFNα-4 as an active ingredient is reduced to 1/10 was administered to test dogs (shiba cross, 2 years 4 months old) with varying administration period to examine the anti-inflammatory effect against Malassezia external otitis was examined. The test dogs used for the examination are as follows.

TABLE 2

| Study group | No | Body weight (Kg) |
| --- | --- | --- |
| Control group | C01 | 9.9 |
| | C02 | 6.8 |
| | C03 | 9.5 |
| Treated group | T01 | 10.6 |
| | T02 | 6.7 |
| | T02 | 7.3 |

Figure 5:
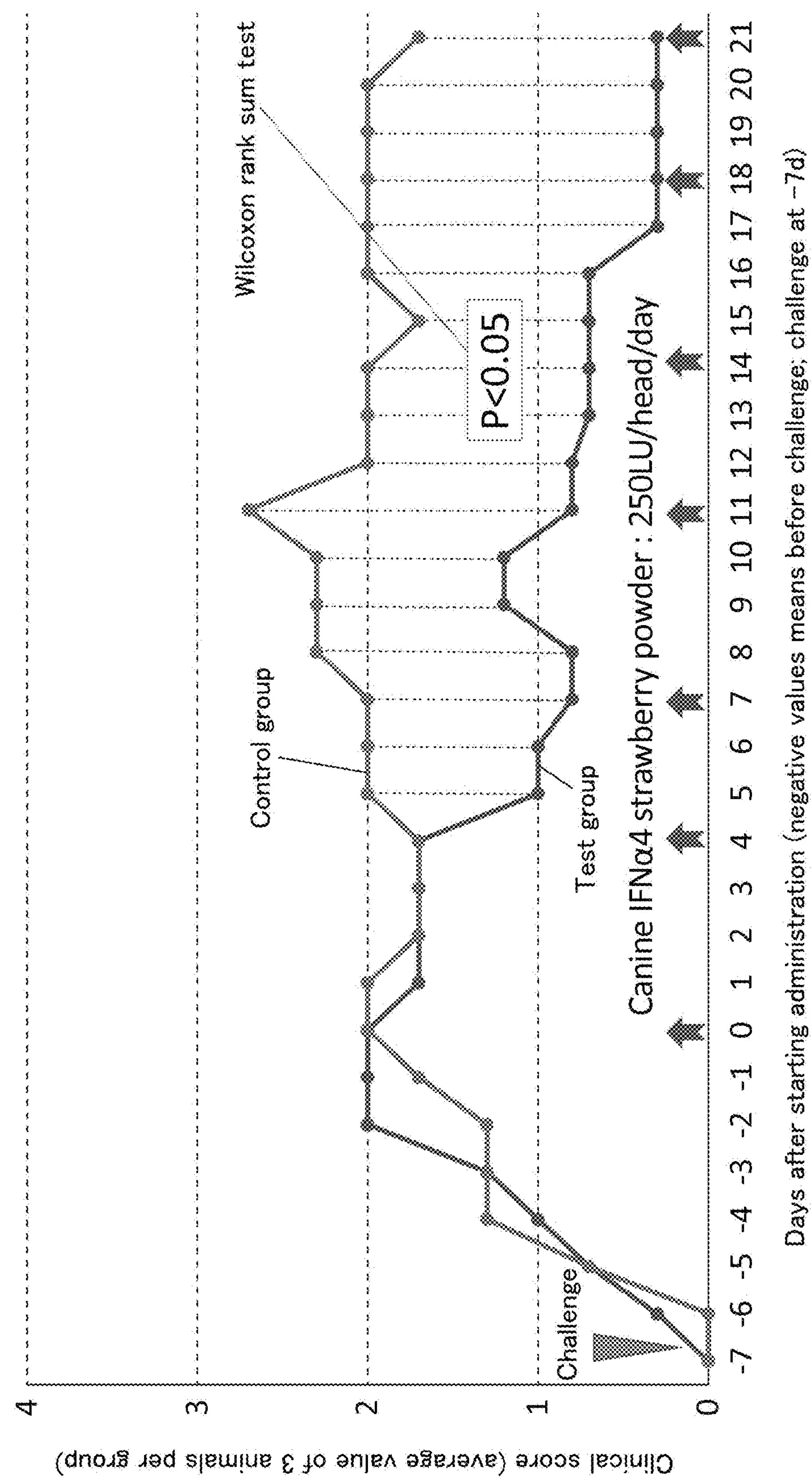
FIG. 5 illustrates transitions of clinical findings for external ears of each group during administration period. IFNα-4 at 2,500 LU/head/day was applied onto gingivae of three test dogs in a treated group twice a week before feeding. Observation findings for the external ear were recorded in comparison with three dogs in a non-treated group.

CaIFNα-4 (250 LU/head) was administered twice a week to three dogs in the treated group with gingival application before feeding (7 times in total), and observation findings for the external ear were recorded in comparison with the control group (non-treated group). As in Example 7, four symptoms of pruritus, redness in external ear, bad odor of external ear, dark brown coloring of cerumen characteristic of Malassezia external otitis were scored. FIG. 5 illustrates transitions of the clinical findings for external ears of each group during administration period. The onset of gingival application of the test drug in the treated group resulted in significant alleviation in the symptoms compared to the non-administration control group, and the difference in clinical score was significant as compared with the non-treated group.

Figure 6:
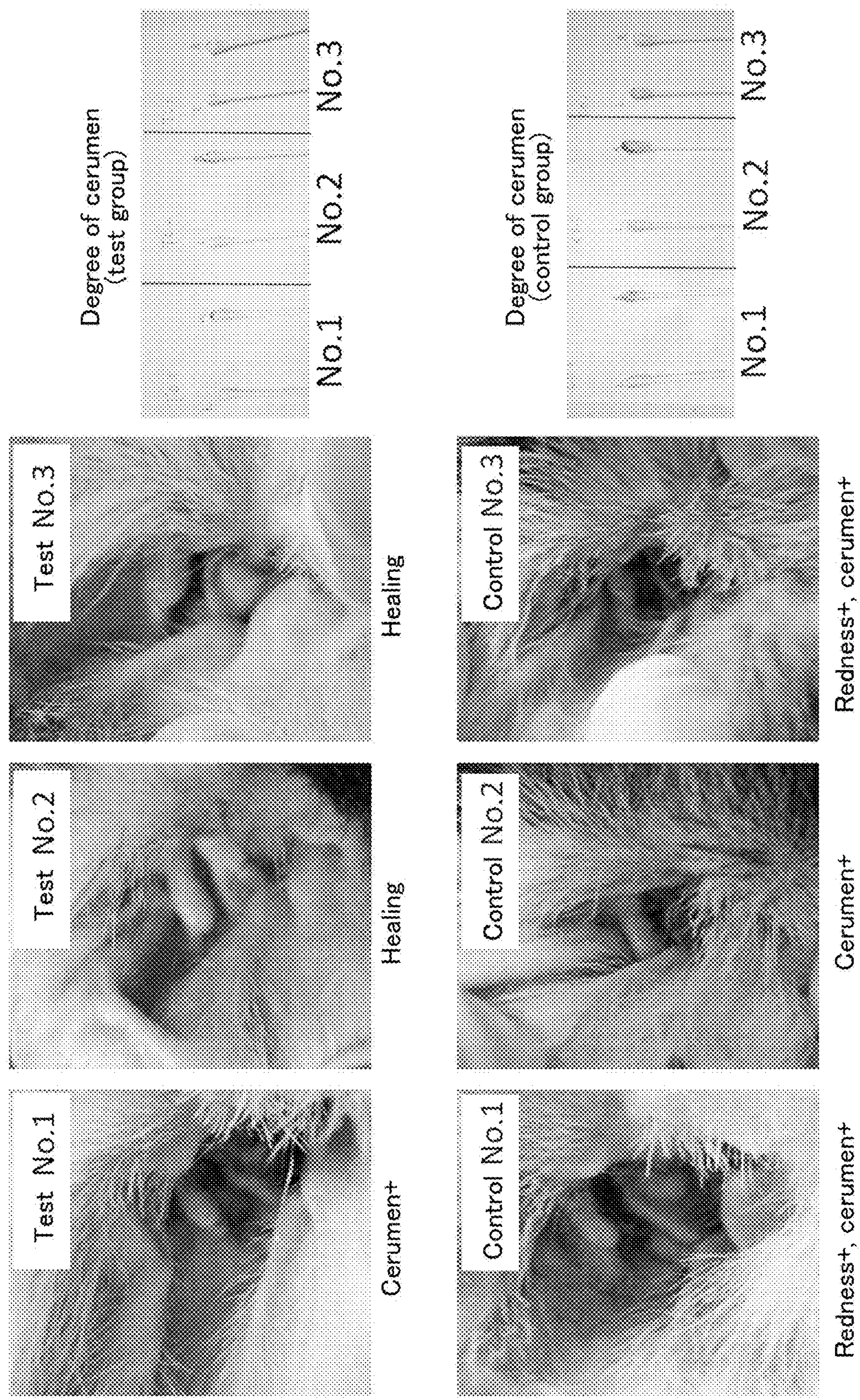
FIG. 6 illustrates photographs depicting findings for external ears and degree of cerumen browning in each test dog on the 21st day after the start of administration.

FIG. 6 illustrates photographs depicting findings for external ears and degree of brown color of cerumen of each test dog on the 21st day after the start of administration. Similarly to the results of the administration test of Example 7, local lesions in the external ear in the treated group were clearly reduced.

From the above, it was revealed that administration of canine interferon-α via gingiva application illustrated an anti-inflammatory effect on intractable external otitis caused by Malassezia species even if the concentration adopted in Example 7 was reduced to 1/10.

INDUSTRIAL APPLICABILITY

The present invention is useful for prevention or treatment of chronic intractable external otitis in animals. In pets such as dogs and cats, prevention and treatment of chronic intractable external otitis generally has become an important issue. The effect of the composition of the present invention can be obtained by applying it to the gingiva.

[Sequence Listing]

The invention claimed is:

1. A method for treating chronic intractable external otitis, comprising orally administering interferon-α.

2. The method according to claim 1, comprising orally administering a composition comprising interferon-α and a chewable carrier or a paste carrier.

3. The method according to claim 2, wherein the method of treatment is treating chronic intractable external otitis, which is Malassezia external otitis.

4. The method according to claim 1, wherein 0.5 to 25,000 laboratory units (LU)/day/kg of body weight of interferon-α is orally administered.

5. The method according to claim 4, wherein the method of treatment is treating chronic intractable external otitis, which is Malassezia external otitis.

6. The method according to claim 1, wherein chronic intractable external otitis is Malassezia external otitis.

* * * * *

SEQUENCE LISTING

```
<160> NUMBER OF SEQ ID NOS: 6

<210> SEQ ID NO 1
<211> LENGTH: 561
<212> TYPE: DNA
<213> ORGANISM: Canis sp.

<400> SEQUENCE: 1
```

```
atggccctgc cctgctcctt ctcggtggcc ctggtgctgc tcagctgcca ctccctgtgc     60

tgtctggctt gcgacctgcc cgacacccac agcctgcgca actggagggt cctgacgctc    120

ctgggacaga tgaggagact ctccgccagc tcttgtgacc actacaccac tgactttgcc    180

ttccccaagg aactgtttga tggccagcgg ctccaggagg cgcaagccct ctctgtggtc    240

cacgtgatga cccagaaggt cttccacctc ttctgcacga acatgtcctc tgctccttgg    300

aacatgaccc tcctggaaga attgtgctcg ggctctctg agcagctgga tgacctggat    360

gcctgtcccc tgcaggaggc agggctggcc gagacccccc tcatgcatga agactccacc    420

ctgaggacct acttccaaag gatctccctc tacctgcaag acaggaacca cagcccgtgt    480

gcctgggaga tggtccgagc agaaatcggg agatccttct tctccttgac catcttgcaa    540

gaaagagtaa ggaggaggaa a                                              561


<210> SEQ ID NO 2
<211> LENGTH: 187
<212> TYPE: PRT
<213> ORGANISM: Canis sp.

<400> SEQUENCE: 2

Met Ala Leu Pro Cys Ser Phe Ser Val Ala Leu Val Leu Leu Ser Cys
1               5                   10                  15

His Ser Leu Cys Cys Leu Ala Cys Asp Leu Pro Asp Thr His Ser Leu
            20                  25                  30

Arg Asn Trp Arg Val Leu Thr Leu Leu Gly Gln Met Arg Arg Leu Ser
        35                  40                  45

Ala Ser Ser Cys Asp His Tyr Thr Thr Asp Phe Ala Phe Pro Lys Glu
    50                  55                  60

Leu Phe Asp Gly Gln Arg Leu Gln Glu Ala Gln Ala Leu Ser Val Val
65                  70                  75                  80

His Val Met Thr Gln Lys Val Phe His Leu Phe Cys Thr Asn Met Ser
                85                  90                  95

Ser Ala Pro Trp Asn Met Thr Leu Leu Glu Glu Leu Cys Ser Gly Leu
            100                 105                 110

Ser Glu Gln Leu Asp Asp Leu Asp Ala Cys Pro Leu Gln Glu Ala Gly
        115                 120                 125

Leu Ala Glu Thr Pro Leu Met His Glu Asp Ser Thr Leu Arg Thr Tyr
    130                 135                 140

Phe Gln Arg Ile Ser Leu Tyr Leu Gln Asp Arg Asn His Ser Pro Cys
145                 150                 155                 160

Ala Trp Glu Met Val Arg Ala Glu Ile Gly Arg Ser Phe Phe Ser Leu
                165                 170                 175

Thr Ile Leu Gln Glu Arg Val Arg Arg Arg Lys
            180                 185


<210> SEQ ID NO 3
<211> LENGTH: 22
<212> TYPE: DNA
<213> ORGANISM: Artificial Sequence
<220> FEATURE:
<223> OTHER INFORMATION: synthetic primer sequence for canine IFN-alpha
      4

<400> SEQUENCE: 3

gcaggatcca cgatggccct gc                                              22
```

-continued

```
<210> SEQ ID NO 4
<211> LENGTH: 59
<212> TYPE: DNA
<213> ORGANISM: Artificial Sequence
<220> FEATURE:
<223> OTHER INFORMATION: synthetic primer sequence for canine IFN-alpha
      4

<400> SEQUENCE: 4

gctgagctca aagttcatcc ttatgatgat gatgatgatg tttcctcctc cttactctt      59


<210> SEQ ID NO 5
<211> LENGTH: 4
<212> TYPE: PRT
<213> ORGANISM: Artificial
<220> FEATURE:
<223> OTHER INFORMATION: synthetic peptide with artificially added ERR
      signal sequence

<400> SEQUENCE: 5

Lys Asp Glu Leu
1


<210> SEQ ID NO 6
<211> LENGTH: 4
<212> TYPE: PRT
<213> ORGANISM: Artificial Sequence
<220> FEATURE:
<223> OTHER INFORMATION: synthetic peptide with artificially added ERR
      signal sequence

<400> SEQUENCE: 6

Arg Asp Glu Leu
1
```